United States Patent [19]

Shirkhanzadeh

[11] Patent Number: 5,211,833

[45] Date of Patent: May 18, 1993

[54] METHOD FOR COATING IMPLANTS AND SURGICAL DEVICES MADE OF TITANIUM AND TITANIUM ALLOYS

[75] Inventor: Morteza Shirkhanzadeh, Kingston, Canada

[73] Assignee: Queen's University at Kingston, Kingston, Ontario, Canada

[21] Appl. No.: 735,222

[22] Filed: Jul. 24, 1991

[51] Int. Cl.$^5$ ............................................. C25D 11/26
[52] U.S. Cl. ..................................................... 205/322
[58] Field of Search ......................................... 205/322

[56] References Cited

FOREIGN PATENT DOCUMENTS 82966 3/1990 Japan .

Primary Examiner—T. M. Tufariello
Attorney, Agent, or Firm—Richard J. Hicks

[57] ABSTRACT

A method for coating implantable medical devices, such as orthopaedic prostheses, with a dense, substantially non-porous oxide coating so as to minimize ion release therefrom, and the product of that process is described. The prosthesis is subjected to anodic electrolytic deposition in an alcoholic electrolyte containing alkali metal nitrate or nitric acid. In a preferred embodiment the anodically coated prosthesis is also coated with a bioactive layer of calcium phosphate.

18 Claims, No Drawings

METHOD FOR COATING IMPLANTS AND SURGICAL DEVICES MADE OF TITANIUM AND TITANIUM ALLOYS

FIELD OF INVENTION

This invention relates to a process for forming a thick, dense and biocompatible oxide coating on the titanium and titanium alloy. More particularly this invention relates to a process for coating titanium alloy prosthetic devices so as to minimize ion loss therefrom.

BACKGROUND OF INVENTION

Titanium and its alloys are finding increasing use in medical devices, including heart valves, cardiac pacemakers, bone plates, artificial joints and dental implants. There has been considerable interest, especially in the use of Ti-6Al-4V alloy, for orthopaedic implants because of its biocompatibility and fatigue strength. Occasionally, however, metal ions, particularly aluminum ions, have been found in tissue adjacent to titanium implants. Inflammatory and toxic effects associated with such metal release have also been reported. The problem of ion release is particularly of concern in the case of porous-coated implants. It should be noted that a prevailing method of achieving component stability of orthopaedic joint replacement devices is now by the use of porous-coated implants. High surface area, porous-coated implants have been shown to exhibit higher corrosion rates compared with conventional non-porous implants. There has also been some question of the wear resistance of Ti-6Al-4V against ultra high molecular polyethylene (UHMPE). For example, the wear rate has been observed to be about 100 times that encountered with the stainless steel or cast CO-Cr-Mo alloy under the same conditions of testing.

A number of surface modification techniques have been developed in the past to improve the corrosion performance and the wear resistance of Ti surgical implant alloys. These include plasma spraying $TiO_2$, nitriding, ion implantation and special passivation techniques. The main disadvantage of ion implantation techniques is that the wear resistant layer or the corrosion resistant coating obtained by these methods are not sufficiently thick. As a result, the implant may lose its surface properties in the long term. For example, it has been shown that an ion-implanted layer in pure titanium, initially about 0.3 micrometer thick was worn to a remaining thickness of about 0.1 micrometer in the contact zone, at the completion of one million cycles wear test. Another problem with the ion-implantation technique is that the homogeneous ion implantation on complex substrates is difficult to realize.

Thick $TiO_2$ coatings can be applied to titanium alloys by plasma spray technique but there are major problems associated with this method. The plasma spray deposition technique is a line of sight process which produces a non-uniform coating when applied to porous surfaces. Non-uniform coatings can create a local exposure of the metal and may provoke a local increase in metal ion release. Because of the high temperature involved, the technique has also the potential to alter the microstructure of the metal substrate and may weaken the implant material's resistance to fatigue. Plasma spray techniques are also very expensive as only about 15% of the relatively expensive $TiO_2$ powder sprayed is actually deposited on the target. Titanium oxide coatings may also be formed on titanium and titanium alloys by anodization at relatively low temperatures. However, in most cases, conventional anodizing solutions described in the prior art do not have any dissolving power on the oxide layer formed during anodization. Therefore, the oxide layer thickness does not exceed more than 1 to 2 microns. This is, clearly, not a sufficient oxide thickness necessary for the long term performance of implants and surgical devices. Anodizing solutions, having fluoride and chloride containing ions with strong dissolving power on the oxide, have also been developed which allow the formation of relatively thick but porous oxide coatings. The porous oxide coatings have important industrial applications such as (a) eliminating the tendency of titanium towards seizure by retaining lubricants and (b) promoting the bonding between titanium and polymeric coatings such as adhesives and paints. However, there are major concerns associated with the application of these coatings to prosthetic devices for use in the human body. Scanning electron microscopy has shown that these coatings are, indeed, highly porous. The pores are formed by localized fluoride or chloride attack on the oxide as it is formed during anodization. As a result, toxic compounds containing fluoride, chloride, Ti, or a combination of these are formed which may be retained in the pores of the oxide during the anodizing process. These compounds may gradually leach out in the body and interfere with normal tissue growth near the implant. Certainly, the first requirement for any material to be placed in the body is that it should be biocompatible and not cause any adverse reactions.

OBJECT OF INVENTION

It is, therefore, an object of this invention to overcome the shortcomings of the prior art, by providing a process for producing on titanium or titanium alloys oxide coatings that are sufficiently thick, dense, substantially non-porous, biocompatible, and which can be formed at relatively low temperatures. Another object of this invention is to provide a process for coating a surgical implant made of titanium zirconium and alloys thereof with a dense, smooth, adherent oxide coating.

BRIEF STATEMENT OF INVENTION

By one aspect of this invention there is provided a process for producing a protective, thick, non-porous and biocompatible oxide coating on a metal substrate selected from the group consisting of titanium, zirconium and alloys thereof, comprising anodically forming said oxide coating by immersing a selected said substrate in an electrolyte comprising at least one of an alkali metal nitrate and nitric acid dissolved in an alcohol having the formula ROH where R is selected from an alkyl group having 1 to 4 carbon atoms, an aryl group and mixtures thereof, and passing a current through said electrolyte for a sufficient time to anodically deposit said coating on said substrate.

By another aspect of this invention there is provided a metal substrate, selected from the group consisting of titanium, zirconium and alloys thereof, having a protective, thick, non-porous and biocompatible oxide coating deposited thereon.

DETAILED DESCRIPTION OF PREFERRED EMBODIMENTS OF INVENTION

The process of anodizing the metal substrate and particularly surgical devices, implants and the like is conducted, according to the present invention, in an electrolyte solution comprising an alkali metal nitrate or nitric acid dissolved in an alcohol, preferably methanol or ethanol. Other alcohols, having a general formula ROH, where R is an alkyl group having 1–4 carbon atoms or an aryl group and mixtures thereof, may also be used. It is important that the water content of the electrolyte is kept at a level less than 10% by volume, and preferably less than 2% by volume. The anodizing voltage is from about 1 volt to about 20 volts, and preferably from 1 to 5 volts. The concentration of alkali metal nitrate or nitric acid in the solvent should be at a level that results in a current density of from 2 to 20 mA per square centimeter, and preferably from 4 to 8 mA per square centimeter. Examples of salts which may be used in this process include sodium nitrate, potassium nitrate, and mixtures thereof.

The temperature of the electrolyte may vary from about room temperature up to a point reasonably below the boiling point of the electrolyte. Suitable cathode materials for the process of this invention include titanium, zirconium or an alloy based on one or both of these two metals. The anodizing process, according to this invention, may be carried out under constant DC current or constant DC voltage or a combination of these two methods. During the anodizing, current or voltage may be gradually increased to a pre-determined level and then kept constant.

Adherent, dense, and uniform coatings of titanium oxide can be obtained by the process of this invention. The thickness of the oxide layer, which is governed by the quantity of current and duration of the process, can be varied between 1 micron and 40 microns. Auger electron spectroscopy (AES) results have indicated that the coating is mainly composed of titanium oxide. Without wishing to be bound by any theory, it is believed that small quantities of complex phases of Ti-N and Ti-C are also formed in the oxide. Scanning electron microscopy has shown that coating is highly dense and without defects or porosity. Auger election spectroscopy and energy dispersive spectroscopy have indicated that the coating is substantially free of vanadium which improves biocompatability.

The process of this invention is applicable both to pure titanium and to titanium-based alloys, e.g., those containing alloying constituents such as aluminium, vanadium, molybdenum, palladium, yttrium and zirconium, as well as other film forming metals such as zirconium and its alloys.

The article to be anodized, according to the process of this invention, may be suitably cleaned or given a cleaning pre-treatment through various means using conventional procedures. The article may have a porous surface or may be roughened by, for example, sand blasting, etching or other conventional methods prior to the anodizing process. The surface of the article may also have micro or macro textures prior to the anodizing process.

A characteristic feature of the process of this invention is that a thick oxide coating with an extremely smooth surface (mirror finish) can be obtained on articles made of titanium, zirconium, and alloys of these metals, provided that these articles are subjected to a polishing treatment such as hand polishing, glass beading, vapour blasting or electrolytic polishing, prior to the anodizing process. Thick and smooth coatings are of particular interest for a number of biomedical applications. For example, a smooth surface is required to minimize bioadhesion and prevent thrombus formation on the implants that come in direct contact with blood and for temporary or semi-permanent implants (e.g. ventilation tubes, percutaneous devices for drug infusion and other similar devices). A smooth and hard surface with a low friction coefficient is also in demand for human joint prostheses where the wear rate should be minimized.

The corrosion resistance of the articles anodized by the process of this invention may be further improved by conventional anodizing under constant current or constant potential in, for example, a phosphoric acid anodizing bath. The corrosion resistance of the articles anodized by the process of this invention may also be further improved by heat treatment in a vacuum or under oxygen atmosphere at high temperature.

The biocompatibility and bioactivity of the metal implants anodized according to the process of this invention, may be further improved by depositing a layer of bioactive calcium phosphate compounds on the anodized implant. This can be achieved by, for example, plasma spraying bioactive calcium phosphate coatings such as hydroxyapatite on the anodized implant. Bioactive calcium phosphate compounds can also be electrodeposited on the anodized titanium implants at relatively low temperatures according to the method described in U.S. Pat. No. 650,189 filed Feb. 4, 1991 and commonly assigned herewith the disclosure of which is incorporated herein by reference. Thick and adherent coatings of bioactive calcium phosphate have been formed by this method on the oxide coated titanium implants. It should be noted that titanium oxide is a semiconductor and therefore permits electrodeposition of bioactive calcium phosphate to occur. Without wishing to be bound by any theory, it is believed that during the electrodeposition process of calcium phosphate, a strong chemical bond develops between the calcium phosphate and titanium oxide coating on the implant. The strength of this bond may be further improved by a hydrothermal or heat treatment process in air or vacuum at a temperature between 100° and 800° C.

EXAMPLE 1

An anodizing electrolyte was prepared by adding 10 gr of sodium nitrate ($NaNO_3$) powder to 1 liter of methanol (HPLC grade). The electrolyte was stirred by a magnetic stirrer for 2 hours to enhance the dissolution of sodium nitrate powder. The electrolyte was then transferred to a conventional electrolytic cell having a capacity of 1 liter. The cell was fitted with a titanium cathode electrode having an exposed surface area of 10 square centimeters. The surface of a titanium alloy (Ti-6Al-4V) sample 5 cm long, 1 cm wide and 2 mm thick was mechanically ground on both sides and then cleaned with methanol in an ultrasonic bath for 15 minutes. The sample was then washed with distilled water and dried in a stream of air. The sample was then immersed in the anodizing electrolyte and used as the anode of the cell. The anode and the cathode were then connected to the positive and negative terminals of a DC power supply, respectively. The cell voltage was increased gradually until a current density of 7 mA per square centimeter was reached. The current was then kept constant at this level for 2 hours. This experiment was conducted at room temperature. After 2 hours anodizing, the anodized sample was removed from the cell, washed with distilled water and dried in a stream of air for 10 minutes. The anodized sample obtained had a matt black colour and the oxide coating was firmly adhered to the substrate. Electron microscopic examination of the cross section of the anodized sample was carried out using a scanning electron microscope. At relatively high magnification (×1,500), it was observed that the oxide coating was dense without detectable defects. The oxide thickness was 20 microns.

EXAMPLE 2

An anodizing electrolyte identical to the electrolyte in Example 1 was used. A titanium alloy (Ti-6Al-4V) sample 5 cm long, 1 cm wide, and 2 mm thick was mechanically polished successively until a mirror finish was obtained. The sample was then anodized at a constant current of 7 mA per square centimeter for 2 hours. The anodized sample obtained had shiny black colour and a mirror finish surface. Scanning electron microscopic exmaination of the cross section of the anodized sample revealed that the oxide coating was dense, having a thickness of 20 microns. The outer surface of the oxide was extremely smooth.

EXAMPLE 3

An anodizing electrolyte identical to the electrolyte in Example 1 was used. A titanium alloy (Ti-6Al-4V) sample, 5 cm long, 1 cm wide, and 2 mm thick was roughened on both sides by blasting it with steel grit (average particle diameter of 0.5 mm) and then cleaned with methanol in an ultrasonic bath for 15 minutes. The sample was then anodized at a constant current of 7 mA per sqare centimeter for 2 hours. The anodized sample obtained had a matt black surface. The oxide coating was uniform and well adhered to the substrate.

EXAMPLE 4

A titanium alloy (Ti-6Al-4V) sample was anodized according to the procedure described in Example 1. The anodized sample was then heat treated at 800° C. in air for 1 hour. The colour of the sample changed from black to a yellowish colour. X-ray diffraction of the sample revealed that the heat treatment procedure resulted in a further crystallization of the oxide coating. The heat treatment procedure also improved the corrosion resistance of the sample.

EXAMPLE 5

A titanium alloy (Ti-6Al-4V) sample was anodized according to the procedure described in Example 1. The anodized sample was then further anodized in 0.1 M phosphoric acid bath for one hour at a constant cell voltage of 20 volts. This treatment resulted in a decrease in the leakage current and improved the corrosion resistance of the sample.

EXAMPLE 6

A titanium alloy (Ti-6Al-4V) sample, 5 cm long, 1 cm wide and 2 mm thick was roughened on both sides by blasting it with steel grit and then cleaned with methanol in an ultrasonic bath for 15 minutes. The sample was then anodized as in Example 3. The anodized sample was then coated with a layer of bioactive calcium phosphate compound by electrolysing at 65° C. for 2 hours at −1,300 mV (versus a Standard Calomel Electrode) in a bath at pH 4.4 containing 20 g calcium phosphate tribasic and 58.5 g sodium chloride per liter of distilled water. Scanning electron microscopy examination of the coated sample revealed that the calcium phosphate coating structure comprised an interlocking network of fine and plate-like crystals in the range of 2 to 5 microns in size. The calcium phosphate coating also had fine micro pores in the order of 2 to 5 microns. The coating was continuous and uniform and firmly adhered to the anodized substrate.

EXAMPLE 7

A titanium alloy (Ti-6Al-4V) sample, 5 cm long, 1 cm wide and 2 mm thick was roughened and coated as in Example 6. The sample was then heat treated at 500° C. in air for 1 hour. This treatment improved the adhesion of the bioactive calcium phosphate coating to the anodized substrate.

I claim:

1. A process for producing a protective, dense, non-porous and biocompatible oxide coating on a metal substrate selected from the group consisting of titanium, zirconium and alloys thereof, comprising anodically depositing said oxide coating by immersing a selected said substrate in an electrolyte comprising at least one of an alkali metal nitrate and nitric acid dissovled in an alcohol having the formula ROH where R is selected from an alkyl group having 1 to 4 carbon atoms, an aryl group and mixtures thereof, and passing a current through said electrolyte for a sufficient time to anodically deposit said coating on said substrate.

2. The process of claim 1, wherein said alcohol is selected from methanol, ethanol and mixtures thereof.

3. The process of claim 1, wherein said alcohol contains less than 10% by volume water.

4. The process of claim 1, wherein said alkali metal nitrate is selected from sodium nitrate, potassium nitrate and mixtures thereof.

5. The process of claim 1, wherein an anodizing voltage of less than 20 volts is applied.

6. The process of claim 1, wherein the anodizing current is from about 2 to about 20 mA per square centimeter.

7. The process of claim 1, wherein the concentration of said at least one of alkali metal nitrate and nitric acid is adjusted below the saturation level thereof so as to provide a minimum current density of 2 mA/sq cm.

8. The process of claim 1, wherein the anodizing process is continued for a sufficient time to form an oxide coating having a thickness from about 1 to about 40 microns.

9. A process according to claim 8, wherein the surface of the metal substrate is polished to a mirror finish prior to anodizing.

10. A process according to claim 8, wherein the said coated metal substrate is subjected to a heat treatment step at a temperature in the range of 300° to 800° C.

11. A process according to claim 10, wherein said heat treatment is effected under vacuum conditions.

12. A process according to claim 10, wherein said heat treatment is effected in an oxygen atmosphere.

13. A process according to claim 1, including anodizing said coated metal substrate in a phosphoric acid bath under selected conditions so as to improve corrosion resistance thereof.

14. A process according to claim 1, including coating said coated metal substrate with a layer of bioactive calcium phosphate.

15. A process according to claim 14, wherein said bioactive calcium phosphate coating is applied by plasma spraying.

16. A process according to claim 14, wherein said bioactive calcium phosphate coating is applied by electrodeposition.

17. An oxide coated metal substrate made by the process of claim 1.

18. An oxide and calcium phosphate coated metal substrate made by the process of claim 14.

* * * * *